(12) United States Patent
Nikawa (10) Patent No.: US 8,304,379 B2
(45) Date of Patent: Nov. 6, 2012

(54) SILICON COMPOUND-CONTAINING SOLIDIFIED DETERGENT COMPOSITION AND METHOD FOR PRODUCING THE SAME

(75) Inventor: Hiroki Nikawa, Hiroshima (JP)

(73) Assignee: Hiroshima University (JP)

( * ) Notice: Subject to any disclaimer, the term of this patent is extended or adjusted under 35 U.S.C. 154(b) by 0 days.

(21) Appl. No.: 12/670,368

(22) PCT Filed: Jul. 4, 2008

(86) PCT No.: PCT/JP2008/062164
§ 371 (c)(1),
(2), (4) Date: Apr. 2, 2010

(87) PCT Pub. No.: WO2009/013991
PCT Pub. Date: Jan. 29, 2009

(65) Prior Publication Data
US 2010/0190683 A1    Jul. 29, 2010

(30) Foreign Application Priority Data

Jul. 25, 2007 (JP) ................................ 2007-193786

(51) Int. Cl.
*C11D 9/36* (2006.01)
(52) U.S. Cl. ........ 510/384; 510/116; 510/191; 510/199; 510/238; 510/356; 510/362; 510/421; 510/422; 510/466; 510/504
(58) Field of Classification Search ............... 510/116, 510/191, 199, 238, 356, 384, 421, 422, 466, 510/504, 362
See application file for complete search history.

(56) References Cited

U.S. PATENT DOCUMENTS

| | | | |
|---|---|---|---|
| 4,005,028 A | | 1/1977 | Heckert et al. |
| 5,411,585 A | * | 5/1995 | Avery et al. ................. 106/287.1 |
| 5,959,014 A | * | 9/1999 | Liebeskind et al. ........... 524/389 |
| 6,632,805 B1 | * | 10/2003 | Liebeskind et al. ............. 514/63 |
| 2002/0111282 A1 | * | 8/2002 | Charaf et al. .................. 510/130 |
| 2003/0109395 A1 | * | 6/2003 | Neumiller ..................... 510/246 |
| 2006/0193816 A1 | * | 8/2006 | Elfersy et al. ............... 424/70.28 |
| 2006/0281662 A1 | * | 12/2006 | Cheung et al. ................ 510/504 |
| 2007/0065475 A1 | * | 3/2007 | Elfersy .......................... 424/405 |
| 2007/0227557 A1 | | 10/2007 | Ohlhausen et al. |
| 2009/0197786 A1 | * | 8/2009 | Perry et al. .................... 510/191 |
| 2010/0093666 A1 | * | 4/2010 | Moses et al. .................... 514/63 |
| 2010/0235975 A1 | * | 9/2010 | Cheung et al. .................... 4/222 |

FOREIGN PATENT DOCUMENTS

| JP | 63195200 A | 8/1988 |
|---|---|---|
| JP | 05295002 A | 11/1993 |
| JP | 2001288062 A | 10/2001 |
| JP | 2004209241 A | 7/2004 |
| JP | 2006213709 A | 8/2006 |
| JP | 2007016201 A | 1/2007 |
| JP | 2007031290 A | 2/2007 |
| JP | 2007146134 A | 6/2007 |
| WO | WO-9956714 A1 | 11/1999 |
| WO | 03/085075 A1 | 10/2003 |
| WO | 2007/148053 A1 | 12/2007 |

OTHER PUBLICATIONS

International Search Report, Application No. PCT/JP2008/062164, Mailed Sep. 8, 2008, 3 pages.
State Intellectual Property Office of China, "Notification of the First Office Action," dated Mar. 16, 2011.
State Intellectual Property Office of China, "Notification of the Second Office Action," dated Aug. 10, 2011.
European Office Communication for Application No. 08777879.1, dated May 24, 2012, 8 pages.

* cited by examiner

*Primary Examiner* — Charles Boyer
(74) *Attorney, Agent, or Firm* — Nutter McClennen & Fish LLP; Thomas J. Engellenner (57) ABSTRACT

According to the present invention, a solidified detergent composition is provided. The solidified detergent composition is characterized by having a reduced-pressure dried substance obtained by reduced-pressure drying a solution of (a) a silicon-containing compound with the addition of (b) at least one of surfactant to the silicon-containing compound, or a reduced-pressure dried substance obtained by reduced-pressure drying a solution of (a) a silicon-containing compound and (b) at least one of surfactant added to the resultant reduced-pressure dried substance, the silicon-containing compound being represented by the following general formula (1):

[Chemical Formula 1]

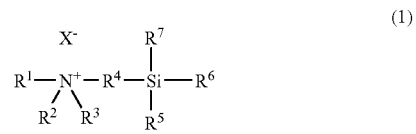

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion) and the surfactant being selected from the group consisting of (b1) a cationic surfactant (but excluding the above silicon-containing compound) and (b2) a nonionic surfactant.

24 Claims, 3 Drawing Sheets

FIG. 2

SILICON COMPOUND-CONTAINING SOLIDIFIED DETERGENT COMPOSITION AND METHOD FOR PRODUCING THE SAME

TECHNICAL FIELD

This invention relates to a solidified detergent composition which is superior in antimicrobial properties and is allowed to re-dissolve with water by reduced-pressure drying, and relates to a method for producing the same.

BACKGROUND ART

With the advent of the aging society, dental materials, in particular, false tooth users increase and then usage of the false tooth detergent (cleaner) also increases, but a false tooth detergent of various compositions is used. In addition, hygiene intention to living environment has improved, and hygiene intention or antimicrobial intention to tableware, spectacles, kitchen sink, kitchen circumference, toilet stool, restroom circumference, bathtub, bathroom circumference, wash bowl, washroom circumference, textile goods or clothing has been raised.

If the antimicrobial detergents used for these are classified by the component system, the detergents can be classified as a component system consisting of a principal component of either a peroxide, hypochlorous acid, enzyme, acid, crude drug, silver-based inorganic antimicrobial agent or disinfectant, alternatively as a component system combined two or more kinds components together. And the concrete composition varies in the antimicrobial detergent belonging to the same component system.

Because the function from both the washing performance and sterilization performance is required for an antimicrobial detergent, the reason why various antimicrobial detergents are used in this way is that the components exerting each action are often combined together to comprise a detergent. In addition, such a antimicrobial detergent that can make use of the higher washing performance or sterilization performance or the short washing time is required, and the demand is particularly remarkable in a false tooth detergent.

For such a demand, for example, International Publication WO 99/56714 A1 bulletin describes that as to the conventional false tooth detergent, the sodium lauryl sulfate has the superior washing performance and foaming action, but there is a problem that the effect of sodium lauryl sulfate is diminished due to the combined component. In order to solve the problem, WO 99/56714 discloses a false tooth detergent which contains the sodium lauryl sulfate and an antimicrobial metal ion such as silver, copper, zinc ion, etc. and does not disturb a function of sodium lauryl sulfate and can improve further the sterilization performance.

Japanese Patent Application Laid-Open No. 2001-288062 bulletin describes that an acid false tooth detergent is preferable for removal of the denture plaque, but if a false tooth detergent is acid, gingival material changes its shape or color, and it is apprehended that metal material goes black and therefore, many detergents are adjusted to present the neutrality, and there is a problem that the washing performance of false tooth detergent is diminished. In order to solve the problem, Japanese Patent Application Laid-Open No. 2001-288062 discloses a granular or tablet-shaped false tooth detergent, which comprises an acidic fast-dissolving portion containing acid and persulfate, and an alkaline slow-dissolving portion containing at least one perborate or percarbonate and a carbonate, in which the false tooth detergent is combined with false tooth lavation and the liquidity of the water can be changed from low pH to high pH.

Japanese Patent Application Laid-Open No. 2004-209241 bulletin discloses an antimicrobial material, in which an antimicrobial substance such as octadecyl trimethoxysilane, γ-aminopropyl triethoxysilane, octadecyl dimethyl (3-trimethoxysilyl propyl) ammonium chloride, etc. is immobilized on the surface. Japanese Patent Application Laid-Open No. 2004-209241 discloses also that the antimicrobial material can be used in the dental application such as a false tooth, implant, crown, bridge, orthodontic bracket, wire, etc., but the detergent composition containing these antimicrobial components itself is not disclosed.

By the improvement of such a detergent, the detergent having enhanced washing performance and sterilization performance came to be provided. However, in the conventional detergent, there was a problem that even if the dental materials such as in particular, false tooth, implant, crown, bridge, orthodontic bracket, dental wire were washed to clean, it was not able to prevent the denture plaque from forming on the false tooth surface again while these dental materials, in particular, a false tooth was installed into the oral cavity to use. Furthermore, the washing performance of dental materials, in particular, improved false tooth washing performance is improved, such a detergent is desired. In addition, as to the detergent for antimicrobial action to tableware, spectacles, kitchen sink, kitchen circumference, toilet stool, restroom circumference, bathtub, bathroom circumference, wash bowl, washroom circumference, textile goods or clothing, the similar antimicrobial performance, washing performance and performance about its persistence are desired.

Further, Japanese Patent Application Laid-Open No. 2007-146134 bulletin describes that in view of the above-mentioned problems, the aim is to enhance the washing performance and sterilization performance, and to improve the antimicrobial performance, washing performance and those persistences after washing the object article to be washed, and in the dental materials such as in particular, false tooth, implant, crown, bridge, orthodontic bracket, dental wire, in particular, false tooth, the aim is to provide a detergent composition which comprises both the antibacterial performance and washing performance that can prevent the denture plaque from reembodying on the false tooth surface while the false tooth is installing into the oral cavity. In addition, the aim of Japanese Patent Application Laid-Open No. 2007-146134 is also to provide a false tooth detergent composition which can easily give the antimicrobial performance to a false tooth without giving the special burden or feeling of discomfort in particular a false tooth user.

Furthermore, the aim of Japanese Patent Application Laid-Open No. 2007-146134 is to provide a detergent composition in which the similar antimicrobial performance, washing performance and performance about its persistence can meet a demand as the detergent for a tableware, spectacles, kitchen sink, kitchen circumference, toilet stool, restroom circumference, bathtub, bathroom circumference, wash bowl, washroom circumference, textile goods or clothing.

DISCLOSURE OF INVENTION

However, the antimicrobial detergent described in Japanese Patent Application Laid-Open No. 2007-146134 bulletin was able to exist only in a liquid state, and when the antimicrobial silyl-based compound is solidified, it becomes a polymer and was not able to dissolve as the detergent again. Therefore, it is a problem to be solved by this invention to powder—solidify an antimicrobial detergent in the form of liquid such as octadecyldimethyl (3-trimethoxysilyl) ammonium chloride, etc. and to make it re-dissoluble in tap water and thereby enabling the antimicrobial detergent described in Japanese Patent Application Laid-Open No. 2007-146134 to utilize as powder cleansing agent and solidity cleansing agent.

In order to achieve the above-mentioned task, this invention provides a solidified detergent composition, which is characterized in that the composition has a reduced-pressure dried substance obtained by reduced-pressure drying a solution of (a) a silicon-containing compound with the addition of (b) at least one of surfactant to the silicon-containing compound, or the composition has a reduced-pressure dried substance obtained by reduced-pressure drying a solution of (a) a silicon-containing compound and (b) at least one of surfactant added to the resultant reduced-pressure dried substance, the silicon-containing compound is represented by the following general formula (1):

[Chemical Formula(Chem.) 1]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion) and the surfactant is selected from the group consisting of (b1) a cationic surfactant (but excluding the above silicon-containing compound) and (b2) a nonionic surfactant.

According to the invention, the solidification (powderization) of the detergent composition which included a silicon-containing compound such as octadecyl dimethyl (3-trimethoxysilyl) ammonium chloride, etc. was accomplished and it enabled the antimicrobial agent to use for a powder detergent or solidity detergent, and a powder detergent and solidity detergent which an antimicrobial effect was added to were provided.

BEST MODE FOR CARRYING OUT THE INVENTION

In the invention, the detergent contained, as a principal ingredient, the silicon-containing compound such as octadecyl dimethyl (3-trimethoxysilyl propyl) ammonium chloride (hereinafter referred to as QAS) which was a silane compound having quaternary ammonium salt that had an antimicrobial property and was able to be immobilized on a surface of material. And, the detergent was used to wash daily clothing-tableware-restroom-bath, etc., thereby removing a surface dirt, and immobilizing the silicon-containing compound such as QAS, and in accordance with the more washing, the more antimicrobial effect lasted for a long term was obtained and such an effect was achieved.

But it is known that QAS gelates during the storage for a long term in water solvent, and its effect falls. Furthermore, QAS exists as liquid and the solidification is very difficult, and therefore, it is disturbed to put QAS to practical use as a detergent. Accordingly, in the invention, a cationic surfactant or nonionic surfactant was added to an undiluted solution of QAS, the protective action intended to stabilize the solution component, at the same time, ethanol or t-butyl alcohol was added to the solvent of QAS to make it liable to an azeotropic state with methanol which was a solvent component, the reduced-pressure drying was performed under low temperature (about −30° C. to −60° C.), thereby enabling the antimicrobial detergent which was able to exist only a liquid state heretofore to solidify (powder). Furthermore, the solidified detergent composition of the invention can dissolve in tap water easily. In addition, there is an advantageous point that by solidifying this agent, the volume of this agent can be decreased to a hundredth or less. For example, if this agent is desired to use as a detergent with final concentration of the 20 times dilution, assuming that this agent is desired to enter to about 10 mL of water for washing, 500 mL of this agent is necessary. In addition, as to the false tooth detergent, if it is desired to regulate to be 20 times dilution at 200 mL, 10 mL of this agent is necessary, but such volume of 10 mL is substantially enormous compared to a current solid form false tooth detergent. Thus, in order to attempt a compactification in the final form of product, the solidification is also essential requirement, and at the same time, the industrial utility value was greatly enhanced. In this way, the invention has a most remarkable characteristic point that an antimicrobial silicon compound OAS capable of immobilization to a surface of material was solidified (powdered) and come into practical use as a detergent.

QAS, which uses in the embodiments as a usable antimicrobial silicon-containing compound by the invention is the most suitable, but it is not intended to be limited to this compound. The examples of the usable antimicrobial silicon-containing compound in this invention are described in detail later.

The reduced-pressure dried detergent composition of the invention is obtained by reduced-pressure drying a solution of an antimicrobial silicon-containing compound such as QAS or the like with the addition of a surfactant such as a cationic surfactant or nonionic surfactant or the like. Furthermore, the undiluted solution of QAS is commercially available in the form that dissolved in methanol as the solvent, but it is suit- able in the invention to add a lower alcohol such as ethanol or t-butyl alcohol other than a surfactant from the viewpoint of azeotrope as mentioned above.

In the detergent composition of the invention, a surfactant exists, thereby the re-dissolution of reduced-pressure dried detergent composition becomes easy. In addition, even in the point of antimicrobial property, as shown in the following embodiments, the inventors obtained a finding that the antimicrobial activity was lost in the solution which a lyophilized product of the undiluted solution of QAS without existing a surfactant was dissolved again. Furthermore, the reduced-pressure dried detergent composition of the invention is superior in the re-dissolubility to water, and a gelation is not occurred after dissolving, and there is no discouragement in use. In addition, considering the solution in which the reduced-pressure dried detergent composition of the invention was re-dissolved with water, the antimicrobial property almost equal to undiluted solution of QAS was shown.

After that manner, the prepared mixture solution contains an antimicrobial silicon-containing compound, a cationic surfactant or nonionic surfactant, and preferably contains a lower alcohol and the mixture solution is reduced-pressure dried, thereby the solidified detergent composition of the invention can be obtained. This is the reason under the condition of reduced-pressure, the solvent in which an antimicrobial silicon-containing compound dissolves can be removed. Meanwhile, it is preferable as an aspect in the invention that an antimicrobial silicon-containing compound is dissolved in a solution, the solution is frozen, and lyophilized under the reduced-pressure. The condition of the reduced-pressure drying can be properly modified as desired, and preferably the reduced-pressure drying is performed under the condition of low temperature such as about −30° C. to −60° C., thereby the decomposition of the antimicrobial component or the like can be prevented.

The solidified detergent composition of the invention is characterized by having a reduced-pressure dried substance of a solution of (a) a silicon-containing compound with the addition of (b) at least one of surfactant to the silicon-containing compound, or having a reduced-pressure dried substance of a solution of (a) a silicon-containing compound and (b) at least one of surfactant added to the reduced-pressure dried substance, the silicon-containing compound is represented by the following general formula (1):

[Chem. 2]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion) and the surfactant is selected from the group consisting of (b1) a cationic surfactant (but excluding the above silicon-containing compound) and (b2) a nonionic surfactant.

Further, the invention provides a method for producing the solidified detergent composition. As one aspect of the invention, an antimicrobial silicon-containing compound can be dried under the reduced-pressure after adding a cationic surfactant or nonionic surfactant. In addition, as another aspect of the invention, after an antimicrobial silicon-containing compound is dried under the reduced-pressure, a cationic surfactant or nonionic surfactant can be added.

Accordingly, in the invention, a method for producing a solidified detergent composition is also provided, the method is characterized by having the steps of: preparing a solution of (a) a silicon-containing compound with the addition of (b) at least one of surfactant to the silicon-containing compound, the silicon-containing compound is represented by the following general formula (1):

[Chem. 3]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion) and the surfactant is selected from the group consisting of (b1) a cationic surfactant (but excluding the above silicon-containing compound) and (b2) a nonionic surfactant; and reduced-pressure drying the solution.

Furthermore, in the invention, a method for producing a solidified detergent composition is also provided, the method is characterized by having the steps of: reduced-pressure drying a solution of (a) a silicon-containing compound represented by the following general formula (1):

[Chem. 4]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion); and
adding (b) at least one of surfactant to a reduced-pressure dried substance obtained in the above step, the surfactant is selected from the group consisting of (b1) a cationic surfactant (but excluding the above silicon-containing compound) and (b2) a nonionic surfactant.

Furthermore, the invention provides a method for preventing a gelation of the antimicrobial silicon-containing compound. As one aspect of the invention, an antimicrobial silicon-containing compound can be dried under the reduced pressure after adding a cationic surfactant or nonionic surfactant. In addition, as another aspect of the invention, after an antimicrobial silicon-containing compound is dried under the reduced-pressure, a cationic surfactant or nonionic surfactant can be added.

Accordingly, in the invention, a method for preventing a gelation of (a) a silicon-containing compound represented by the following general formula (1):

[Chem. 5]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion) is provided, the method is characterized by having the steps of: preparing a solution of (a) a silicon-containing compound with the addition of (b) at least one of surfactant to the silicon-containing compound, the surfactant is selected from the group consisting of (b1) a cationic surfactant (but excluding the above silicon-containing compound) and (b2) a nonionic surfactant; and reduced-pressure drying the solution.

Moreover, in the invention, a method for preventing a gelation of (a) a silicon-containing compound represented by the following general formula (1):

[Chem. 6]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion) is provided, the method is characterized by having the steps of:

reduced-pressure drying a solution of the silicon-containing compound; and adding (b) at least one of surfactant to a reduced-pressure dried substance obtained in the above step, the surfactant is selected from the group consisting of (b1) a cationic surfactant (but excluding the above silicon-containing compound) and (b2) a nonionic surfactant.

Hereinafter, the constituents of the solidified detergent composition will be explained in detail. The silicon-containing compound usable in the invention is represented by the following general formula (1)

[Chem. 7]

(1)

(wherein R1 shows a hydrocarbon group having 6 or more carbon atom number, R2 and R3 show a lower hydrocarbon group which may be same or different each other, R4 shows a bivalent lower hydrocarbon group, R5, R6 and R7 show a lower alkyl group or lower alkoxy group which may be same or different each other, X shows a halogen ion or organic carbonyloxy ion (organic carboxylate ion)).

Furthermore, among the silicon-containing compound (a) represented in the above-mentioned general formula (1), as a preferable aspect of the silicon-containing compound, R1 of the above-mentioned general formula (1) shows an alkyl group having 10 to 25 carbon atom number, R2 and R3 show a lower alkyl group having 1 to 6 carbon atom number which may be same or different each other, R4 shows a lower alkylene group having 1 to 6 carbon atom number, R5, R6 and R7 show a lower alkyl group having 1 to 6 carbon atom number or a lower alkoxy group which may be same or different each other, X is a halogen ion or organic carbonyloxy ion (organic carboxylate ion).

As a hydrocarbon group having 6 or more carbon atom number in R1, the following groups can be illustrated: a hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, uneicosyl group, doeicosyl group, trieicosyl group, tetraeicosyl group, pentaeicosyl group, etc.

As a lower hydrocarbon group in R2 and R3 which may be same or different, for example, the following groups can be illustrated: methyl group, ethyl group, propyl group, isopropyl group, butyl group, pentyl group, hexyl group, cyclohexyl group, phenyl group, tolyl group, etc.

As a lower alkylene group of R4, the following groups can be illustrated: methylene group, ethylene group, trimethylene group, tetramethylene group, hexamethylene group, etc.

R5, R6 and R7 are a lower alkyl group or a lower alkoxy group which may be same or different each other, and concretely, the following groups can be illustrated: methoxy group, ethoxy group, propoxy group, isopropoxy group, butoxy group, pentyloxy group, hexyloxy group, methyl group, ethyl group, propyl group, isopropyl group, butyl group, pentyl group, hexyl group, etc.

As X, the following can be illustrated: a halogen ion such as chloride ion, bromine ion, etc.; organic carbonyloxy ion (organic carboxylate ion) such as methyl carbonyloxy ion (acetate ion), ethyl carbonyloxy ion (propionate ion), phenyl carbonyloxy ion (benzoate ion), etc.

As silicon-containing compound (a), concretely, the following compounds can be illustrated: octadecyl dimethyl (3-trimethoxysilyl propyl) ammonium chloride, octadecyl diethyl (3-trimethoxysilyl propyl) ammonium chloride, octadecyl dimethyl (2-trimethylsilyl ethyl) ammonium chloride, octadecyl dipropyl (4-trimethoxysilyl butyl) ammonium acetate, octadecyl dimethyl (3-triethoxysilyl propyl) ammonium chloride, octadecyl dimethyl (3-triisopropoxysilyl propyl) ammonium chloride, octadecyl dimethyl (3-triethylsilyl propyl) ammonium chloride, octadecyl dimethyl (3-triisopropylsilyl propyl) ammonium chloride, heptadecyl dimethyl (3-trimethoxysilyl propyl) ammonium chloride, heptadecyl diisopropyl (2-triethoxysilyl ethyl) ammonium chloride, hexadecyl dimethyl (3-trimethoxysilyl propyl) ammonium chloride, hexadecyl dimethyl (3-trimethoxysilyl propyl) ammonium acetate, pentadecyl dimethyl (3-triethoxysilyl propyl) ammonium chloride.

Preferably, a cationic surfactant (b1) usable for the invention is a cationic surfactant (b11) represented by the following general formula (2):

[Chem. 8]

(2)

(wherein R11 shows a hydrocarbon group having 6 or more carbon atom number, R12, R13 and R14 show a lower hydrocarbon group which may be same or different each other), but preferably, it is a cationic surfactant (b11) excluding the above silicon-containing compound (a), and/or N-cocoyl-arginine ethyl ester pyridone carboxylate salt (b12).

Furthermore, among the cationic surfactants (b11) represented by the above general formula (2), it is preferable that R11 shows an alkyl group having 10 to 25 carbon atom number, R12, R13 and R14 show a lower alkyl group having 1 to 6 carbon atom number which may be same or different each other, Y is a halogen ion or organic carbonyloxy ion (organic carboxylate ion).

As a hydrocarbon group R11 having 6 or more carbon atom number in the cationic surfactant (b11) represented by the above general formula (2), similarly to those illustrated as R1 of the general formula (1) of the above-mentioned silicon-containing compound (a), the hydrocarbon groups having 6 or more carbon atom number can be illustrated in like wise.

As R12, R13 and R14 of the cationic surfactant (b11) represented by the above general formula (2), similarly to those illustrated as R2 and R3 of the general formula (1) of the above-mentioned silicon-containing compound (a), the lower hydrocarbon groups can be illustrated in like wise.

As a cationic surfactant (b11) represented by the above general formula (2), the following compounds can be specifically illustrated. That is, decyl trimethyl ammonium chloride, decyl triethyl ammonium acetate, dodecyl trimethyl ammonium acetate, dodecyl triisopropyl ammonium bromide, tridecyl triethyl ammonium bromide, tetradecyl trimethyl ammonium chloride, tetradecyl triethyl ammonium chloride, tetradecyl tri-n-propyl ammonium chloride, pentadecyl trimethyl ammonium chloride, pentadecyl triethyl ammonium chloride, pentadecyl tri-n-propyl ammonium chloride, hexadecyl trimethyl ammonium chloride, hexadecyl triethyl ammonium chloride, hexadecyl tri-n-propyl ammonium chloride, octadecyl trimethyl ammonium chloride, octadecyl triethyl ammonium chloride, octadecyl tri-n-propyl ammonium chloride, etc. can be listed, and in particular, hexadecyl trimethyl ammonium is most suitable.

Nonionic surfactant (b2) usable for the invention is at least one of nonionic surfactant selected from the group consisting of an alkyl ether or fatty acid ester of polyoxyalkylene glycol containing polyoxyethylene unit or/polioxypropylene unit, sorbitan fatty acid ester and fatty acid monoglyceride.

As a nonionic surfactant (b2), concretely, the following can be illustrated: at least one of nonionic surfactant selected from the group consisting of a monoalkyl ether of polyethylene glycol, monoalkyl ether of polyalkylene glycol containing both polyoxyethylene unit and polyoxypropylene unit, sorbitan laurate, polyoxyethylene sorbitan monolaurate and fatty acid monoglyceride can be illustrated, in particular, the polyoxyethylene sorbitan monolaurate is most suitable.

In addition, from the viewpoint of azeotrope, it is preferable to add a lower alcohol having 10 or less carbon number to the detergent composition of the invention. The lower alcohol is more preferably a lower alcohol having 5 or less carbon number, and for the specific example, the following can be listed: ethanol, t-butyl alcohol, propyl alcohol, n-butyl alcohol, isobutyl alcohol, sec-butyl alcohol, tert-butyl alcohol and pentyl alcohol, etc. Ethanol and t-butyl alcohol are particularly suitable among other things.

In the invention, the quantity of the cationic surfactant (e.g., hexadecyl trimethyl ammonium) to be added is 0.01 mg to 1 mg, preferably 0.05 to 0.5 mg, most preferably 0.1 mg per 1 mL of the solution of the antimicrobial silicon-containing compound (e.g., QAS undiluted solution). Further, in the invention, the quantity of the nonionic surfactant (polyoxyethylene sorbitan monolaurate) to be added is 0.05 mL to 10 mL, preferably 0.1 mL to 5 mL, most preferably 1 mL per 1 mL of the solution of the antimicrobial silicon-containing compound (e.g., QAS undiluted solution). However, the additive amount of the surfactant is not limited to this range.

Further, in the invention, the quantity of the lower alcohol (e.g., ethanol, t-butyl alcohol) to be added is 0.1 mL to 10 mL, more preferably 0.5 mL to 2 mL, most preferably 1 mL. However, the additive amount of the lower alcohol is not limited to this range.

EXAMPLES

The invention will be described by the following embodiments in detail, but the scope of the invention is not intended to limit at all.

Example 1

Attempt to Solidify and Evaluation of Solubility

In the undiluted solution of octadecyl dimethyl (3-trimethoxysilyl propyl) ammonium chloride (hereinafter referred to as QAS) which is an antimicrobial detergent, hexadecyl trimethyl ammonium (hereinafter referred to as HD), which was a cationic surfactant, was added, and for the azeotrope, a sample solution with the addition of acetone or ethanol was prepared, azeotrope was performed at 70° C. However, it did not reach solidification. In the resultant gelated substance, tap water of 5 mL was added, but gelation advanced in many samples highly and solidification was occurred within several minutes to 1 hour, and those were not suitable for practical use (Table 1).

On the other hand, such a phenomenon was not seen when ethanol was added (Table 1). Therefore, in the conditions like the ethanol addition groups, the sample was prepared by using t-butyl alcohol in substitution for ethanol, and lyophilized for 15 hours. As a result, solidification (powderization) by lyophilization was possible in both samples. In addition, the solubility to tap water was good, and after dissolution, gelation or the like has not also happened (Table 2). Furthermore, ethanol or t-butyl alcohol was not added, and in the system which only HD was added, the solubility to tap water was good, and after dissolution, gelation or the like had not also happened (Table 2). In the system which as substitution for HD, a nonionic surfactant, polyoxyethylene sorbitan monolaurate (hereinafter referred to as PO) was added, this system was also examined, and then a similar good result was obtained. On the other hand, in the sample that QAS undiluted solution was lyophilized for 1 hour or 5 hours, solidification of the gel was seen after dissolution (Table 2).

Furthermore, in the case that HD or PO was added after lyophilizing QAS undiluted solution for 15 hours, a good property was also shown without occurring gelation or the like after dissolution (Table 3). On the other hand, gelation was recognized after dissolution when the surfactant such as HD, PO, etc. was not added.

TABLE 1

| | Surfactant | Solvent addition | Azeotrope at 70° | Solubility to tap water |
|---|---|---|---|---|
| QAS undiluted solution | Nothing | Nothing | Gelation • Solidification | Gel→Consolidate |
| QAS | HD | Nothing | Gelation • Solidification | Gel→Consolidate |
| QAS | HD | Acetone | Gelation • Solidification | Gel→Consolidate |
| QAS | HD | Ethanol | Gelation • Solidification | Lightly gelated but no solidification |

TABLE 2

| | Surfactant | Solvent addition | Lyophilization 15 hours | Solubility to tap water | Behavior after dissolution |
|---|---|---|---|---|---|
| QAS undiluted solution | Nothing | Nothing | Powderization (1 hour) | No problem | Gelation Solidification |
| QAS undiluted solution | Nothing | Ethanol | Powderization (5 hours) | No problem | Gelation Solidification |
| QAS | PO | Nothing | Powderization | No problem | No problem |
| QAS | HD | Nothing | Powderization | No problem | No problem |
| QAS | HD | Ethanol | Powderization | No problem | No problem |
| QAS | HD | t-Butyl alcohol | Powderization | No problem | No problem |

TABLE 3

| | Surfactant | Solvent addition | Lyophilization 15 hours | Solubility to tap water | Behavior after dissolution |
|---|---|---|---|---|---|
| QAS undiluted solution | Nothing | Nothing | Powderization | No problem | Gelation Solidification |
| QAS undiluted solution | Nothing | Nothing | PO after powderization | No problem | No problem |
| QAS undiluted solution | Nothing | Nothing | HD after Powderization | No problem (Slight white turbidity) | No problem |

Example 2

Evaluation of Antimicrobial Property for Re-Dissolved Liquid of the Antimicrobial Agent The antimicrobial property was evaluated for the following samples: QAS undiluted solution was solidified, directly, or with the addition of a surfactant, and then it was re-dissolved to prepare the samples. That is, QAS undiluted solution of 1 mL was lyophilized and then solidified, (1) the solidified substance was used directly (only QAS), (2) QAS solidified substance with the addition of PO of 1 mL, (3) QAS solidified substance with the addition of HD of 0.1 mg, the above (1) to (3) substance were dissolved in the distilled water (MQ) of 10 mL, again. Furthermore, at this moment, the solution becomes 10 times dilution. In the sample of 900 μL that serial dilution of each re-dissolution liquid was performed by 10 times more, fungi suspension of *C. albicans* IFO 1385 strain which was adjusted to $1 \times 10^6$ cells/mL of 40 μL was added, and Sabouraud nutrient medium of 1 mL was added and cultured at 37° C. for 72 hours, and examined the antimicrobial properties.

After the visual determination, the antimicrobial properties of the above (1) were approximately similar to control (distilled water) of the lower right portion, and the antimicrobial properties were not recognized at all. Regarding the above (2), the antimicrobial properties were weakly recognized in the solution of 10 times dilution, but the antimicrobial properties were not recognized at the further dilution magnification. Regarding the solution of the above (3), the high antimicrobial properties were recognized even at the dilution magnification of 10 times to 1000 times.

Figure 1:
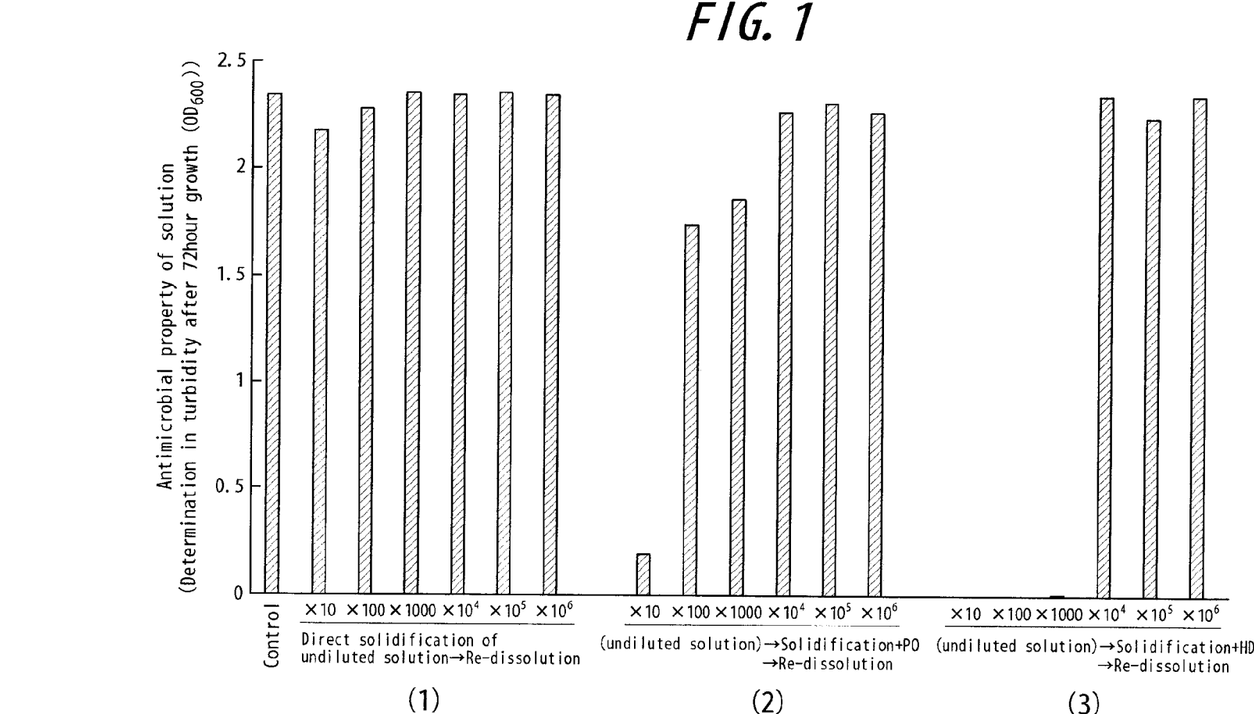
FIG. 1 is a graph showing the evaluated results as to the antimicrobial property of the re-dissolved liquid of the antimicrobial substance in each the systems: octadecyl dimethyl (3-trimethoxysilyl propyl) ammonium chloride is solidified and the resultant solidified substance is re-dissolved without surfactant; the resultant solidified substance is re-dissolved with cationic surfactant; the resultant solidified substance is re-dissolved with nonionic surfactant.

In FIG. 1, these results were quantified. The antimicrobial properties were not recognized in the solution of the above (1) at all (see left graph), whereas as to the case of the solution of the above (2), the number of fungi which were grown was inhibited to about one-tenth of the control in the solution diluted by 10 times (see central graph), and a weak but significant inhibiting effect was obtained even in 100 times, 1000 times dilution solution. In the case of solution of the above (3), the very high antimicrobial properties were shown without recognizing a significant growth of the fungi up to 1000 times dilution (see right graph).

In QAS undiluted solution, without adding a surfactant, or with the addition of a surfactant, the lyophilization and re-dissolution was performed, and the resultant liquid was examined for the antimicrobial properties. Each samples of (1) QAS undiluted solution 1 mL, (2) QAS undiluted solution 1 mL+PO 1 mL, (3) QAS undiluted solution+HD 0.1 mg was prepared, the samples of the above (1) to (3) were lyophilized and then solidified, and re-dissolved in distilled water of 10 mL. Furthermore, at this moment, the solution becomes 10 times dilution. In the sample of 900 μL that serial dilution of each re-dissolution liquid was performed by 10 times more, 40 μL of fungi suspension of *C. albicans* IFO 1385 strain which was adjusted to $1 \times 10^6$ cells/mL was added, and Sabouraud nutrient medium of 1 mL was added and cultured at 37° C. for 72 hours, and examined the antimicrobial properties.

Figure 2:
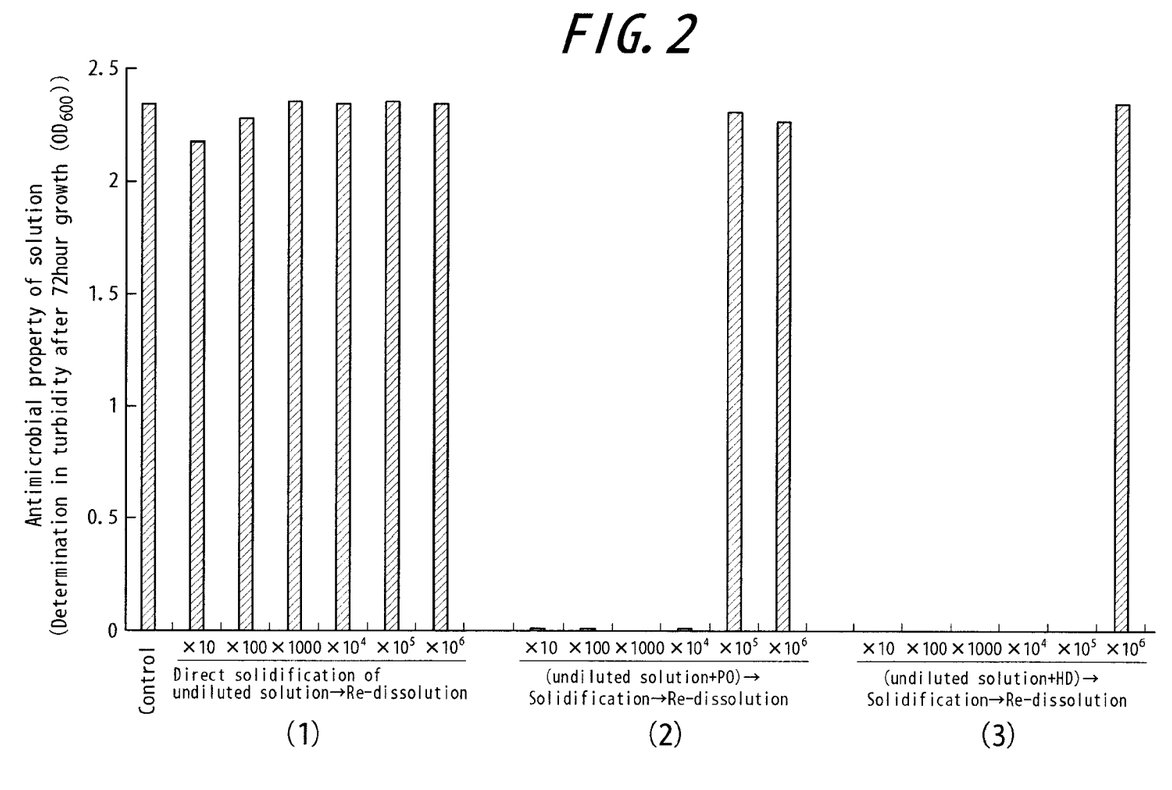
FIG. 2 is a graph showing the evaluated results as to the antimicrobial property of the re-dissolved liquid of the lyophilized solution for each the systems: the solution of octadecyl dimethyl (3-trimethoxysilyl propyl) ammonium chloride as the antimicrobial substance is lyophilized without surfactant; the solution of antimicrobial substance is lyophilized with cationic surfactant; the solution of antimicrobial substance is lyophilized with non-ionic surfactant.

These results were shown in the graphs of FIG. 2. In the solution of the above (1), as was expected, the antimicrobial properties were not recognized at all (see left graph). Whereas as to the case of the solution of the above (2), the very high antimicrobial properties were shown without recognizing a significant growth of the fungi up to $10^4$ diluted solution (see center graph). In the case of solution of the above (3), the very high antimicrobial properties were also shown without recognizing a significant growth of the fungi up to $10^5$ diluted solution (see right graph).

Example 3

Evaluation of Antimicrobial Property in Glass Treated with Re-Dissolved Liquid of the Antimicrobial Agent Each samples of (1) QAS undiluted solution 1 mL, (2) QAS undiluted solution 1 mL+PO 1 mL,(3) QAS undiluted solution+HD 0.1 mg were lyophilized and solidified, and dissolved in distilled water (MQ) of 10 mL again. At this moment, the solution becomes ×10 dilution.

In each the solution, glass test piece of 22×22×0.4 was immersed for 30 minutes. Each glass was referred to as QAS treating glass, PO treating glass, HD treating glass. Each treating glass was washed with water under running water for 5 minutes dried, and then the glass was placed on the bottom face of the 6 well plate and 40 μL of the fungi suspension of C. albicans IFO 1385 strain which was adjusted to $1 \times 10^5$ cells/mL was added to the glass surface, and further, Sabouraud nutrient medium of 5 mL was added and cultured at 37° C. for 72 hours, and then examined the antimicrobial properties.

Untreated glass which was performed no processing, and the treatment using a solution obtained by re-dissolving a substance after solidification of the solution of QAS with the addition of HD (the sample of the above (3)) were compared. At the surface of untreated glass, the colony of the grown fungi was able to be observed, compared to this, the growth of fungi was not recognized at all in the following glass: that is, HD was added in QAS, the resultant solution was solidified by lyophilization, and the solidified substance was re-dissolved to prepare the solution (the solution of the above (3)), the antimicrobial treatment of glass was performed by the solution.

Figure 3:
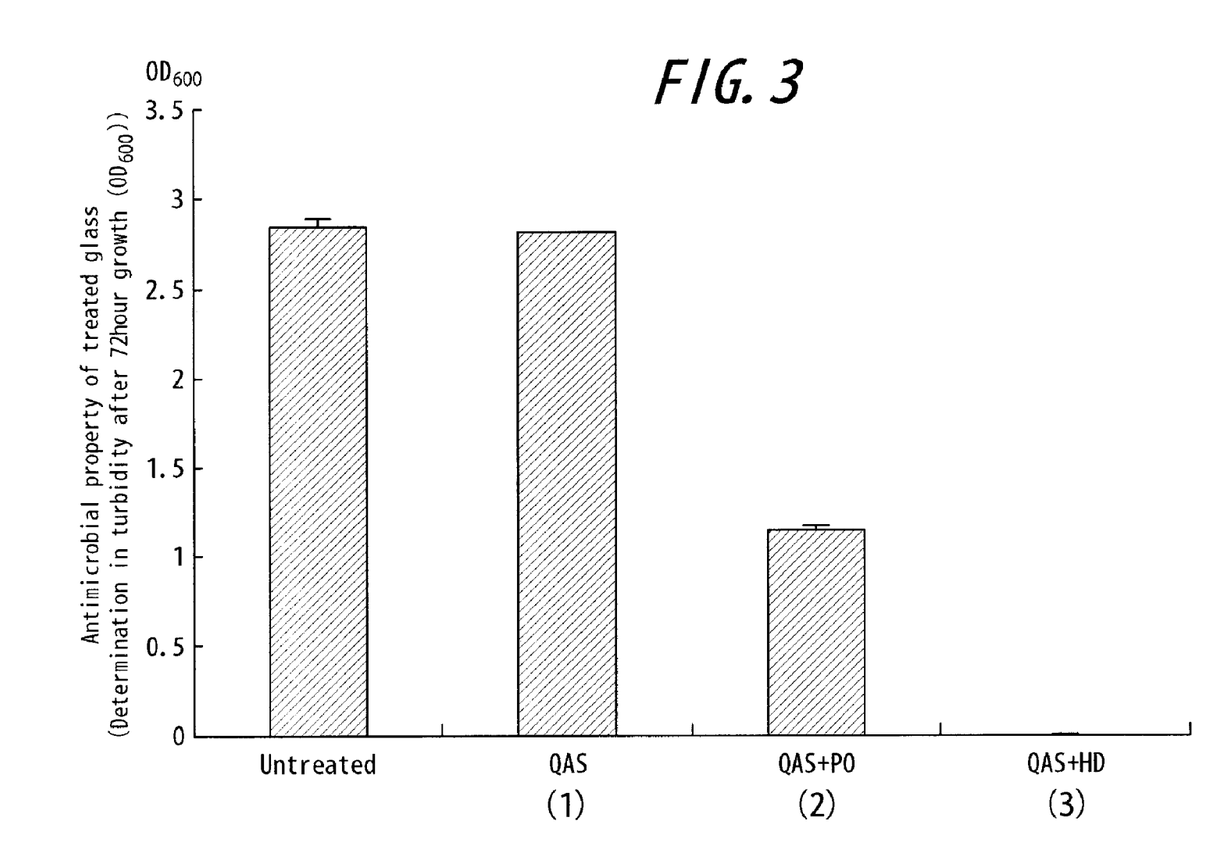
FIG. 3 is a graph showing the evaluated results as to the antimicrobial property of the glass which treated with re-dissolved liquid of the antimicrobial substance in each the systems: octadecyldimethyl (3-trimethoxysilyl propyl) ammonium chloride as the antimicrobial substance without surfactant; the antimicrobial substance with cationic surfactant; the antimicrobial substance with non-ionic surfactant.

FIG. 3 is a graph which quantified antimicrobial properties of the glass treated by the above (1) to (3) solutions. In the treatment by the liquid which QAS undiluted solution was solidified and re-dissolved (the above (1)), the antimicrobial properties were not recognized at all. Compared to this, in the liquid which PO was added, if the liquid was solidified and then re-dissolved (the above (2)), low effect but significant antimicrobial properties were shown and the number of fungi was decreased to about half or less. In the liquid which HD was added, if the liquid was solidified and then re-dissolved (the above (3)), the liquid had extremely high antimicrobial properties, and it was not recognized that the fungi themselves were significantly grown.

The above-mentioned results are summarized as follows. Solidification was easy for the QAS undiluted solution, but antifungal properties were lost when the substance was re-dissolved after solidification. Further, in QAS solution which PO was added, it was recognized that if the solution was solidified and then the solidified substance was re-dissolved, the re-dissolved liquid itself had a weak but significant antifungal properties. Furthermore, the significant antifungal properties were also recognized as to the glass which was treated with the re-dissolved solution. Meanwhile, in QAS solution which HD was added, if the solution was solidified and then the solidified substance was re-dissolved, both the re-dissolved solution itself and the glass which was treated with the re-dissolved solution had a extremely high antifungal properties.

[Industrial Applicability]

By this invention, the solidification (powderization) of the detergent composition which included a silicon-containing compound such as octadecyl dimethyl (3-trimethoxysilyl propyl) ammonium chloride was accomplished and it enabled QAS to use for a powder detergent or solidity detergent. Accordingly, the invention provided a powder detergent and solidity detergent which an antimicrobial effect was added to. Because the detergent composition of this invention has been solidified, the composition can be utilized as powder cleansing agent and solidity cleansing agent, and the composition is superior in point of re-dissolution against tap water. In addition, the compactification of the end product of detergent composition was accomplished by solidification, and the industrial availability of the detergent composition was greatly enhanced.

The invention claimed is:

1. A powdered solidified detergent composition characterized in that the composition comprises a solution of (a) a silicon-containing compound and (b) at least one surfactant, the silicon-containing compound being represented by the following general formula (1):

[Chem. 1]

(1)

wherein $R^1$ is a hydrocarbon group having 6 or more carbon atoms,
$R^2$ and $R^3$ are each a lower hydrocarbon group having 1 to 6 carbon atoms which may be the same or different from each other, $R^4$ is a bivalent lower hydrocarbon group having 1to 6carbon atoms, $R^5$, $R^6$ and $R^7$ are each a lower alkyl group or lower alkoxy group having 1to 6 carbon atoms which may be the same or different from each other, X is a halogen ion or organic carbonyloxy ion and the surfactant being selected from the group consisting of (b1) a cationic surfactant but excluding the above silicon-containing compound and (b2) a nonionic surfactant, the cationic surfactant (b1) is a cationic surfactant (b11) represented by the following general formula (2)

[Chem. 2]

(2)

wherein $R^{11}$ is a hydrocarbon group having 6 or more carbon atoms, $R^{12}$, $R^{13}$ and $R^{14}$ are lower hydrocarbon groups having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride, wherein said composition is characterized in that the composition is dissolvable in water and wherein the silicon-containing compound or the composition comprising a silicon-containing compound and at least one surfactant is a reduced-pressure dried substance, and the reduced-pressure drying of the substance is performed at a temperature of from −30° C. to −60° C.

2. The powdered solidified detergent composition according to claim 1, characterized in that $R^1$ of a silicon-containing compound (a) represented by the above general formula (1) is an alkyl group having 10 to 25 carbon atoms, $R^2$ and $R^3$ are each a lower alkyl group having 1 to 6 carbon atoms which may be the same or different from each other, $R^4$ is a lower alkylene group having 1 to 6 carbon atoms, $R^5$, $R^6$ and $R^7$ are each a lower alkyl group or alkoxy group having 1 to 6 carbon atoms which may be the same or different from each other, and X is a halogen ion or organic carbonyloxy ion.

3. The powdered solidified detergent composition according to claim 1, characterized in that the silicon-containing compound (a) represented by the above general formula (1) is at least one of silicon-containing compound selected from the group consisting of an octadecyl dimethyl (3-trimethoxysilyl propyl) ammonium chloride, octadecyl diethyl (3-trimethoxysilyl propyl) ammonium chloride, octadecyl dimethyl (2-trimethylsilyl ethyl) ammonium chloride, octadecyl dipropyl (4-trimethoxysilyl butyl) ammonium acetate, octadecyl dimethyl (3-triethoxysilyl propyl) ammonium chloride, octadecyl dimethyl (3-triisopropoxysilyl propyl) ammonium chloride, octadecyl dimethyl (3-triethylsilyl propyl) ammonium chloride, octadecyl dimethyl (3-triisopropylsilyl propyl) ammonium chloride, heptadecyl dimethyl (3-trimethoxysilyl propyl) ammonium chloride, heptadecyl diisopropyl (2-triethoxysilyl ethyl) ammonium chloride, hexadecyl dimethyl (3-trimethoxysilyl propyl) ammonium chloride, hexadecyl dimethyl (3-trimethoxysilyl propyl) ammonium acetate, pentadecyl dimethyl (3-triethoxysilyl propyl) ammonium chloride.

4. The powdered solidified detergent composition according to claim 1, characterized in that the silicon-containing compound (a) represented by the above general formula (1) is octadecyl dimethyl (3-trimethoxysilyl propyl) ammonium chloride.

5. The powdered solidified detergent composition according to claim 1, characterized in that $R^{11}$ of the above cationic surfactant (b11) represented by the above general formula (2) is an alkyl group having 10 to 25 carbon atoms, $R^{12}$, $R^{13}$ and $R^{14}$ are each a lower alkyl group having 1 to 6 carbon atoms which may be the same or different from each other, and Y is a halogen ion or organic carbonyloxy ion.

6. The powdered solidified detergent composition according to claim 1 or 5, characterized in that the cationic surfactant (b11) is at least one of surfactant selected from the group consisting of a decyl trimethyl ammonium chloride, decyl triethyl ammonium acetate, dodecyl trimethyl ammonium acetate, dodecyl triisopropyl ammonium bromide, tridecyl triethyl ammonium bromide, tetradecyl trimethyl ammonium chloride, tetradecyl triethyl ammonium chloride, tetradecyl tri-n-propyl ammonium chloride, pentadecyl trimethyl ammonium chloride, pentadecyl triethyl ammonium chloride, pentadecyl tri-n-propyl ammonium chloride, hexadecyl trimethyl ammonium chloride, hexadecyl triethyl ammonium chloride, hexadecyl tri-n-propyl ammonium chloride, octadecyl trimethyl ammonium chloride and octadecyl triethyl ammonium chloride and octadecyl tri-n-propyl ammonium chloride.

7. The powdered solidified detergent composition according to claim 1, characterized in that the above cationic surfactant (b1) is hexadecyl trimethyl ammonium chloride.

8. The powdered solidified detergent composition according to claim 1, characterized in that the nonionic surfactant (b2) is polyoxyethylene sorbitan monolaurate.

9. The powdered solidified detergent composition according to claim 1, characterized in that the composition contains octadecyl dimethyl (3-trimethoxysilyl propyl) ammonium chloride as the above silicon-containing compound (a), and hexadecyl trimethyl ammonium chloride as the above cationic surfactant (b1).

10. The powdered solidified detergent composition according to claim 1, characterized in that the composition contains octadecyl dimethyl (3-trimethoxysilyl propyl) ammonium chloride as the above silicon-containing compound (a), and polyoxyethylene sorbitan monolaurate as the above cationic surfactant (b2).

11. The powdered solidified detergent composition according to claim 1, characterized in that the composition is formed by a process comprising adding a lower alcohol having 10 or less carbon atoms to said solution of a silicon-containing compound and at least one surfactant prior to reduced pressure drying.

12. The powdered solidified detergent composition according to claim 11, characterized in that the lower alcohol is alcohol having 5 or less carbon atoms.

13. The powdered solidified detergent composition according to claim 11, characterized in that the lower alcohol is selected from the group consisting of an ethanol, t-butyl alcohol, propyl alcohol, n-butyl alcohol, isobutyl alcohol, sec-butyl alcohol, tert-butyl alcohol and pentyl alcohol.

14. The powdered solidified detergent composition according to claim 1, characterized in that the composition is re-dissoluble in tap water.

15. A method for manufacturing a powdered solidified detergent composition, characterized in that the method has the steps of:
preparing a solution of (a) a silicon-containing compound with the addition of (b) at least one of surfactant to the silicon-containing compound, the silicon-containing compound being represented by the following general formula (1):

[Chem. 4]

(1)

wherein $R^1$ is a hydrocarbon group having 6 or more carbon atoms,
$R^2$ and $R^3$ are each a lower hydrocarbon group having 1 to 6 carbon atoms which may be the same or different from each other, $R^4$ is a bivalent lower hydrocarbon group having 1 to 6 carbon atoms, $R^5$, $R^6$ and $R^7$ are each a lower alkyl group or lower alkoxy group having 1 to 6 carbon atoms which may be the same or different from each other, X is a halogen ion or organic carbonyloxy ion and the surfactant being selected from the group consisting of (b1) a cationic surfactant but excluding the above silicon-containing compound and (b2) a nonionic surfactant, the above cationic surfactant (b1) is a cationic surfactant (b11) represented by the following general formula (2)

[Chem. 2]

(2)

wherein $R^{11}$ is a hydrocarbon group having 6 or more carbon atoms, $R^{12}$, $R^{13}$ and $R^{14}$ are lower hydrocarbon groups having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one of nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride, and reduced-pressure drying the solution at −30° C. to −60° C. wherein said composition is characterized in that the composition is dissolvable in water.

16. A method for manufacturing a powdered solidified detergent composition, characterized in that the method has the steps of:

reduced-pressure drying a solution of (a) a silicon-containing compound represented by the following general formula (1):

[Chem. 5]

(1)

wherein $R^1$ is a hydrocarbon group having 6 or more carbon atoms, $R^2$ and $R^3$ are each a lower hydrocarbon group having 1 to 6 carbon atoms which may be the same or different from each other, $R^4$ is a bivalent lower hydrocarbon group having 1 to 6 carbon atoms, $R^5$, $R^6$ and $R^7$ are each a lower alkyl group or lower alkoxy group having 1 to 6 carbon atoms which may be the same or different from each other, X is a halogen ion or organic carbonyloxy ion the reduced-pressure drying of the substance is performed at −30° C. to −60° C., and adding (b) at least one of surfactant to a reduced-pressure dried substance obtained in the above step, the surfactant being selected from the group consisting of (b1) a cationic surfactant but excluding the above silicon-containing compound and (b2) a nonionic surfactant, the above cationic surfactant (b1) is a cationic surfactant (b11) represented by the following general formula (2)

[Chem. 2]

(2)

wherein $R^{11}$ is a hydrocarbon group having 6 or more carbon atoms, $R^{12}$, $R^{13}$ and $R^{14}$ are lower hydrocarbon groups having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one of nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride wherein said composition is characterized in that the composition is dissolvable in water.

17. The method according to claim 15 or 16, characterized in that the composition further contains a lower alcohol having 10 or less carbon atoms.

18. A method for preventing a gelation of (a) a silicon-containing compound represented by the following general formula (1):

[Chem. 6]

(1)

wherein $R^1$ is a hydrocarbon group having 6 or more carbon atoms, $R^2$ and $R^3$ are each a lower hydrocarbon group having 1 to 6 carbon atoms which may be the same or different from each other, $R^4$ is a bivalent lower hydrocarbon group having 1 to 6 carbon atoms, $R^5$, $R^6$ and $R^7$ are each a lower alkyl group or lower alkoxy group having 1 to 6 carbon atoms which may be the same or different from each other, X is a halogen ion or organic carbonyloxy ion characterized in that the method has the steps of:

preparing a solution of (a) the silicon-containing compound with the addition of (b) at least one of surfactant to the silicon-containing compound, the surfactant being selected from the group consisting of (b1) a cationic surfactant but excluding the above silicon-containing compound and (b2) a nonionic surfactant, the above cationic surfactant (b1) is a cationic surfactant (b11) represented by the following general formula (2)

[Chem. 2]

(2)

wherein $R^{11}$ is a hydrocarbon group having 6 or more carbon atoms, $R^{12}$, $R^{13}$ and $R^{14}$ are lower hydrocarbon groups having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one of nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride, and reduced-pressure drying the solution at −30° C. to −60° C.

19. A method for preventing a gelation of (a) a silicon-containing compound represented by the following general formula (1):

[Chem. 7]

(1)

wherein $R^1$ is a hydrocarbon group having 6 or more carbon atoms, $R^2$ and $R^3$ are each a lower hydrocarbon group having 1 to 6 carbon atoms which may be the same or different from each other, $R^4$ is a bivalent lower hydrocarbon group having 1 to 6 carbon atoms, $R^5$, $R^6$ and $R^7$ are each a lower alkyl group or lower alkoxy group having 1 to 6 carbon atoms which may be the same or different from each other, X is a halogen ion or organic carbonyloxy ion characterized in that the method has the steps of:

reduced-pressure drying a solution of the silicon-containing compound at −30° C. to −60° C.; and adding (b) at least one of surfactant to a reduced-pressure dried substance obtained in the above step, the surfactant being selected from the group consisting of (b1) a cationic surfactant but excluding the above silicon-containing compound and (b2) a nonionic surfactant, the above cationic surfactant (b1) is a cationic surfactant (b11) represented by the following general formula (2)

[Chem. 2]

(2)

wherein $R^{11}$ is a hydrocarbon group having 6 or more carbon atoms, $R^{12}$, $R^{13}$ and $R^{14}$ are lower hydrocarbon groups having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one of nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride.

20. The method according to any claim 18 or 19, characterized in that the composition further contains a lower alcohol having 10 or less carbon atoms.

21. A powdered solidified detergent composition characterized in that the composition comprises a reduced-pressure dried substance of a solution of (a) a silicon-containing compound with the addition of (b) at least one of surfactant to the silicon-containing compound, the silicon-containing compound being represented by the following general formula (1):

[Chem. 1]

(1)

wherein $R^1$ is a hydrocarbon group having 6 or more carbon atoms, $R^2$ and $R^3$ are each a lower hydrocarbon group having 1 to 6 carbon atoms which may be the same or different from each other, $R^4$ is a bivalent lower hydrocarbon group having 1 to 6 carbon atoms, $R^5$, $R^6$ and $R^7$ are each a lower alkyl group or lower alkoxy group having 1 to 6 carbon atoms which may be the same or different from each other, X is a halogen ion or organic carbonyloxy ion and the surfactant being selected from the group consisting of (b1) a cationic surfactant but excluding the above silicon-containing compound and (b2) a nonionic surfactant, the cationic surfactant (b1) is a cationic surfactant (b11) represented by the following general formula (2)

[Chem. 2]

(2)

wherein $R^{11}$ is a hydrocarbon group having 6 or more carbon atoms, $R^{12}$, $R^{13}$ and $R^{14}$ are lower hydrocarbon groups having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one of nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride, the reduced-pressure drying of the substance is performed at −30° C. to −60° C., wherein the powdered solidified detergent composition further contains a lower alcohol having 5 or less carbon atoms.

22. The powdered solidified detergent composition according to claim 21, characterized in that the lower alcohol is selected from the group consisting of an ethanol, t-butyl alcohol, propyl alcohol, n-butyl alcohol, isobutyl alcohol, sec-butyl alcohol, tert-butyl alcohol and pentyl alcohol.

23. A powdered solidified detergent composition characterized in that the composition comprises a reduced-pressure dried substance of a solution of (a) a silicon-containing compound, and (b) at least one of surfactant added to the reduced-pressure dried substance, the silicon-containing compound being represented by the following general formula (1)

[Chem. 3]

(1)

wherein $R^1$ is a hydrocarbon group having 6 or more carbon atoms,
$R^2$ and $R^3$ are each a lower hydrocarbon group having 1 to 6 carbon atoms which may be the same or different from each other, $R^4$ is a bivalent lower hydrocarbon group having 1 to 6 carbon atoms, $R^5$, $R^6$ and $R^7$ are each a lower alkyl group having 1 to 6 carbon atoms or lower alkoxy group having 1 to 6 carbon atoms which may be the same or different from each other, X is a halogen ion or organic carbonyloxy ion and
the surfactant being selected from the group consisting of (b1) a cationic surfactant but excluding the above silicon-containing compound) and (b2) a nonionic surfactant the above cationic surfactant (b1) is a cationic surfactant (b11) represented by the following general formula (2)

[Chem. 4]

(2)

wherein $R^{11}$ is a hydrocarbon group having 6 or more carbon atoms, $R^{12}$, $R^{13}$ and $R^{14}$ are each a lower hydrocarbon group having 1 to 6 carbon atoms which may be the same or different from each other, Y is a halogen ion, an organic carbonyloxy ion, or an N-cocoyl-arginine ethyl ester pyridone carboxylate salt (b12), the above nonionic surfactant (b2) is at least one of nonionic surfactant selected from the group consisting of an alkyl ether or fatty acid ester of polyoxyalkylene glycol containing polyoxyethylene unit and/or polyoxypropylene unit, a sorbitan fatty acid ester and fatty acid monoglyceride, the reduced-pressure drying of the substance is performed at −30° C. to −60° C.
wherein the powdered solidified detergent composition further contains a lower alcohol having 5 or less carbon atoms.

24. The powdered solidified detergent composition according to claim 23, characterized in that the lower alcohol is selected from the group consisting of an ethanol, t-butyl alcohol, propyl alcohol, n-butyl alcohol, isobutyl alcohol, sec-butyl alcohol, tert-butyl alcohol and pentyl alcohol.

\* \* \* \* \*